United States Patent [19]

Asano et al.

[11] Patent Number: 5,037,059
[45] Date of Patent: Aug. 6, 1991

[54] X-RAY DIAGNOSTIC DEVICE WITH SAFE AND DURABLE X-RAY TUBE SUSPENSION MECHANISM

[75] Inventors: Kiyoshi Asano; Kiyoaki Inoue; Shunichiro Nishigaki, all of Tochigi, Japan

[73] Assignee: Kabushiki Kaisha Toshiba, Kawasaki, Japan

[21] Appl. No.: 367,346

[22] Filed: Jun. 16, 1989

[30] Foreign Application Priority Data

Jun. 17, 1988 [JP] Japan .............................. 63-150915
Jun. 17, 1988 [JP] Japan .............................. 63-150916

[51] Int. Cl.⁵ .............................................. F16M 13/00
[52] U.S. Cl. .................................. 248/572; 248/330.1; 248/579; 248/610
[58] Field of Search ............ 248/572, 573, 579, 610, 248/320, 330.1, 331, 332, 329, 328

[56] References Cited

U.S. PATENT DOCUMENTS

| 39,602 | 8/1863 | Whipple | 248/572 X |
|---|---|---|---|
| 322,515 | 7/1885 | Young | 248/329 |
| 326,364 | 9/1885 | Weston | 248/329 |
| 2,471,998 | 5/1949 | Berggren | 248/572 |
| 2,578,374 | 12/1951 | Pratt | 248/330.1 |
| 3,032,308 | 5/1962 | Hansen | 248/329 |
| 3,575,368 | 4/1971 | Thomas et al. | 248/572 |
| 3,856,267 | 12/1974 | Flannelly | 248/610 X |
| 3,949,842 | 4/1976 | Kiehn | 248/320 X |

FOREIGN PATENT DOCUMENTS

875227  9/1942  France .................. 248/572

Primary Examiner—David L. Talbott
Attorney, Agent, or Firm—Oblon, Spivak, McClelland, Maier & Neustadt

[57] ABSTRACT

An X-ray diagnostic device with a suspension mechanism for suspending an object in a vertically movable manner, using two suspension wires, which can avoid the shortened durability of the suspension wires, and using windup type springs, which can eliminate possibility for the fall of the suspended object due to the breaking of the windup type springs. The suspension mechanism may includes two suspension wires for holding the suspended object; and single threaded corn pulleys, one for each one of the two suspension wires, for winding the respective suspension wires. The suspension mechanism may also includes a plurality of windup type springs for balancing against gravitational force acting on the suspended object; connection between the plurality of windup type springs such that this connection moves when the plurality of windup type springs are put to be not balanced with respect to each other; and mechanism for preventing the fall of the suspended object by detecting motion of the connection.

6 Claims, 13 Drawing Sheets

X-RAY DIAGNOSTIC DEVICE WITH SAFE AND DURABLE X-RAY TUBE SUSPENSION MECHANISM

BACKGROUND OF THE INVENTION

1. Field of the Invention

The present invention relates to a suspension mechanism for hanging an object over another object and, more particularly, to such a suspension mechanism which is particularly suitable as means for supporting X-ray tube in an X-ray diagnostic device which is to be hung over a patient.

2. Description of the Background Art

Conventionally, a suspension mechanism utilized in an X-ray diagnostic device for supporting an X-ray tube in vertically movable manner is equipped with springs for providing a force that balances gravitational force acting on a suspended object. Such springs can be stretchable solenoid type, compressible solenoid type, or windup type, but for the reason of compactness the windup type is preferred most.

Figure 1:
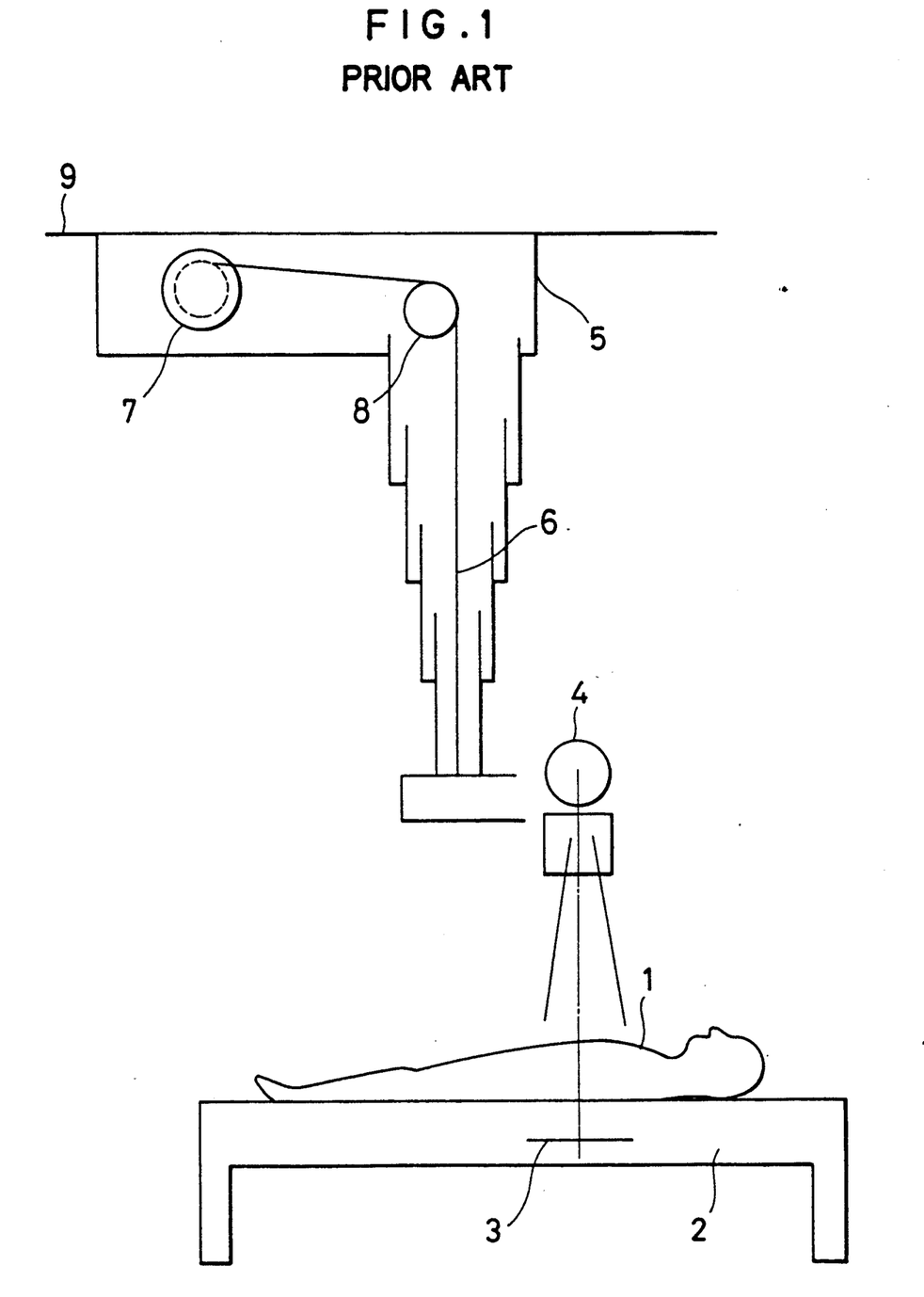
FIG. 1 is a cross sectional view of an example of a conventional suspension mechanism.

FIG. 1 shows an example of such a suspension mechanism in an X-ray diagnostic device, in which a patient 1 is laid on a bed 2, over an X-ray film 3, and a suspended object 4 including an X-ray tube is suspended over the patient 1 by a suspension wire 6 in vertically movable manner which is connected to a balance mechanism 7 through an idler pulley 8. The suspension wire 6, balance mechanism 7 and idler pulley 8 are housed inside a frame 5 attached on a ceiling 9.

Figure 2:
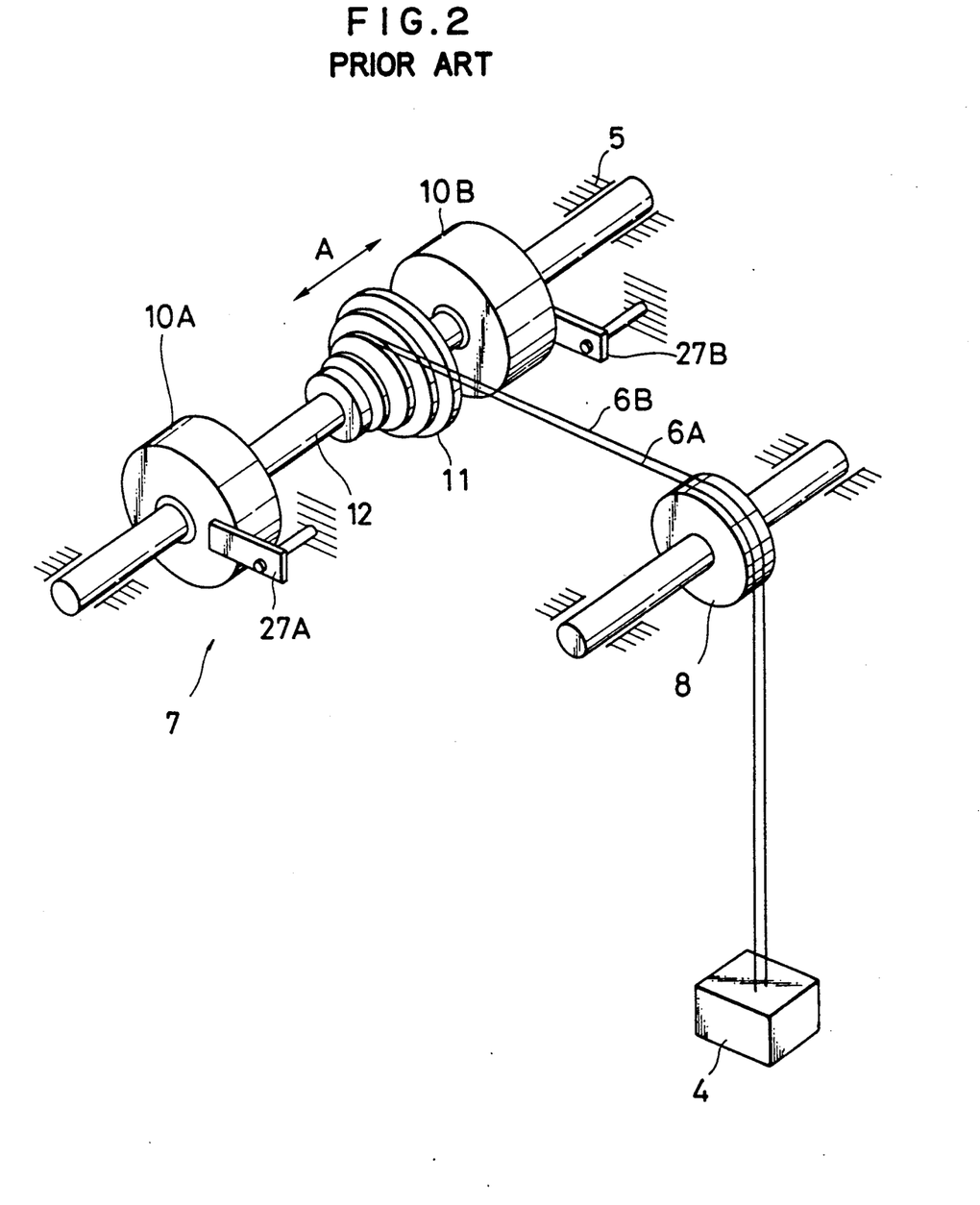
FIG. 2 is a perspective view of a balance mechanism utilized in the suspension mechanism of FIG. 1.

FIG. 2 shows a detail of the balance mechanism 7, in which the suspended object 4 is suspended by left and right suspension wires 6A and 6B to be wound up by a corn pulley 11 attached on a shaft 12 which can rotate by means of windup type springs 13A and 13B (not shown in FIG. 2) contained inside left and right barrels 10A and 10B fixed to the frame 5 by fixing members 27A and 27B, respectively.

Figure 3A:
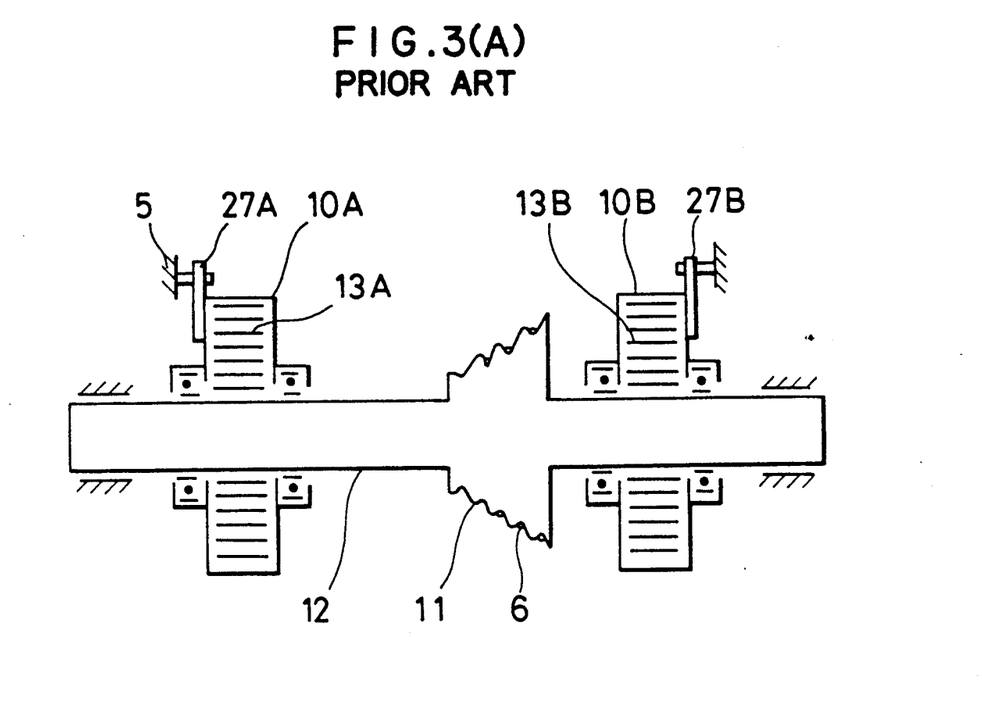
FIGS. 3(A) and 3(B) are transverse and longitudinal cross sectional views, respectively, of barrels and windup type springs housed inside the barrels of the balance mechanism of FIG. 2.
Figure 3B:
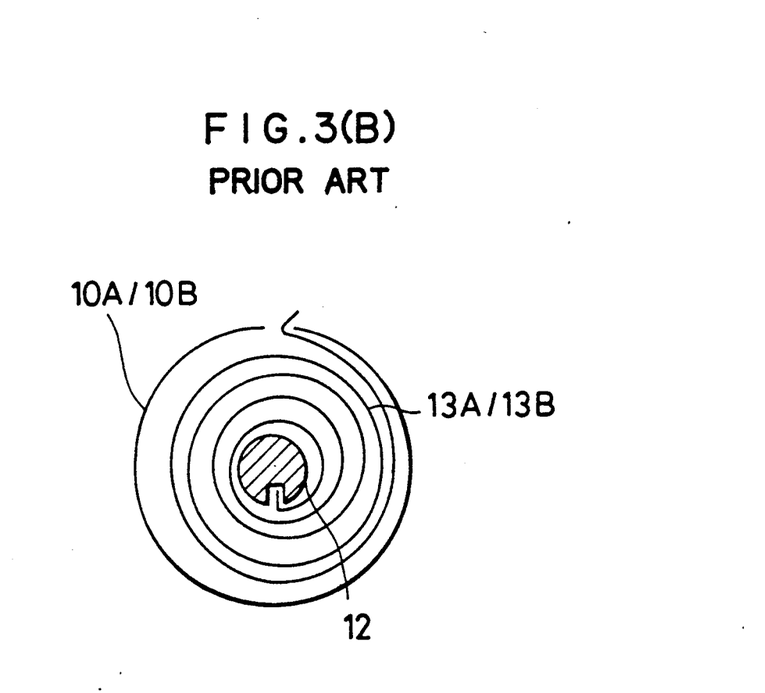

The windup type springs 13A and 13B inside the barrels 10A and 10B are shown in FIGS. 3(A) and 3(B). As shown in FIG. 3(B), one ends of the windup type springs 13A and 13B are hooked on the barrels 10A and 10B, respectively, while the other ends are hooked on the shaft 12, so that torque due to the windup type springs 13A and 13B will be transformed into a power to wind the suspension wires 6A and 6B around the corn pulley 11. Here, the torque due to the windup type springs 13A and 13B, by nature of this type of spring, changes as the shaft 12 rotates, but the corn pulley 11 with changing radii offsets the change in torque, so that the suspended object 4 can be lifted at a constant rate.

Two suspension wires 6A and 6B are provided for the purpose of safety, so that even when one of them are cut off the other one can keep the suspended object 4 from falling. This feature is particularly important in this type of the X-ray diagnostic device in which the X-ray tube have to be suspended over the patient 1, since the fall of the suspended object 4 can cause a serious trouble in such a configuration.

Such a conventional suspension mechanism has two serious problems.

One is that featuring two suspension wires 6A and 6B necessitates double threads on the corn pulley 11, but such double threads increases a fleet angle, which in turn shorten the durability of the suspension wires 6A and 6B.

Figure 4A:
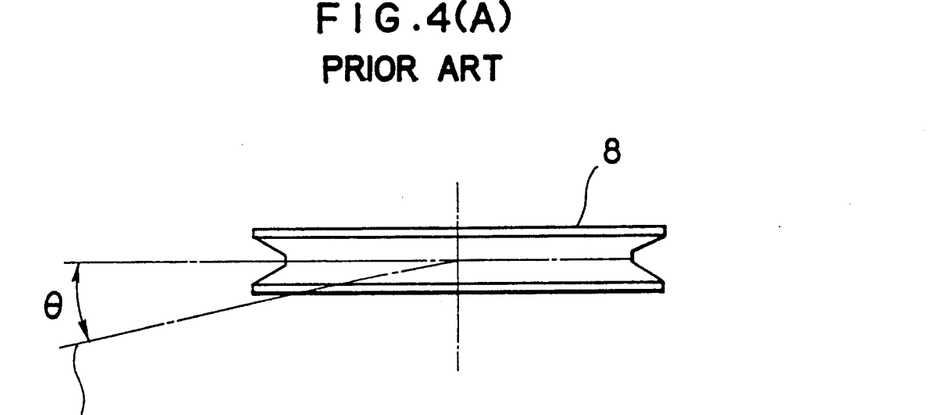
FIGS. 4(A) and 4(B) are transverse and longitudinal views, respectively, of idler pulley and a suspension wire of the balance mechanism of FIG. 2.
Figure 4B:
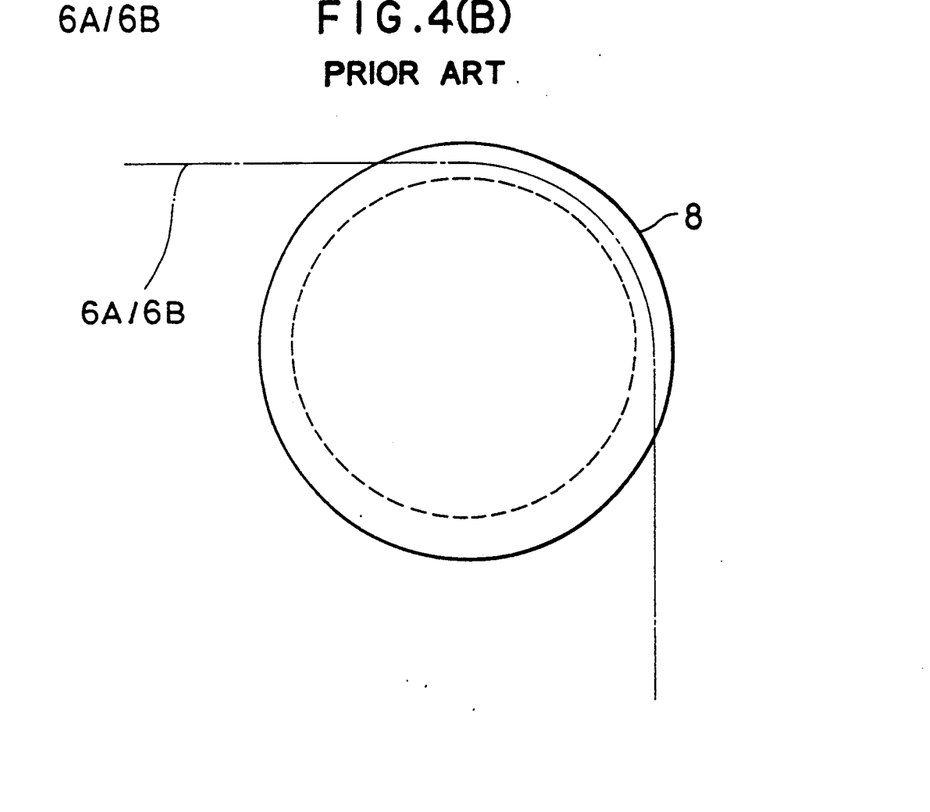

Namely, because of the configuration of the corn pulley 11, location of the suspension wires 6A and 6B slides along the shaft 12 in a direction indicated by an arrow A in FIG. 2, so that when the suspension wires 6A and 6B make contact with the idler pulley 8, the direction of the suspension wires 6A and 6B changes from the beginning of winding to the end of the winding by a so called fleet angle $\Theta$, as can be seen from FIGS. 4(A) and 4(B).

Figure 5:
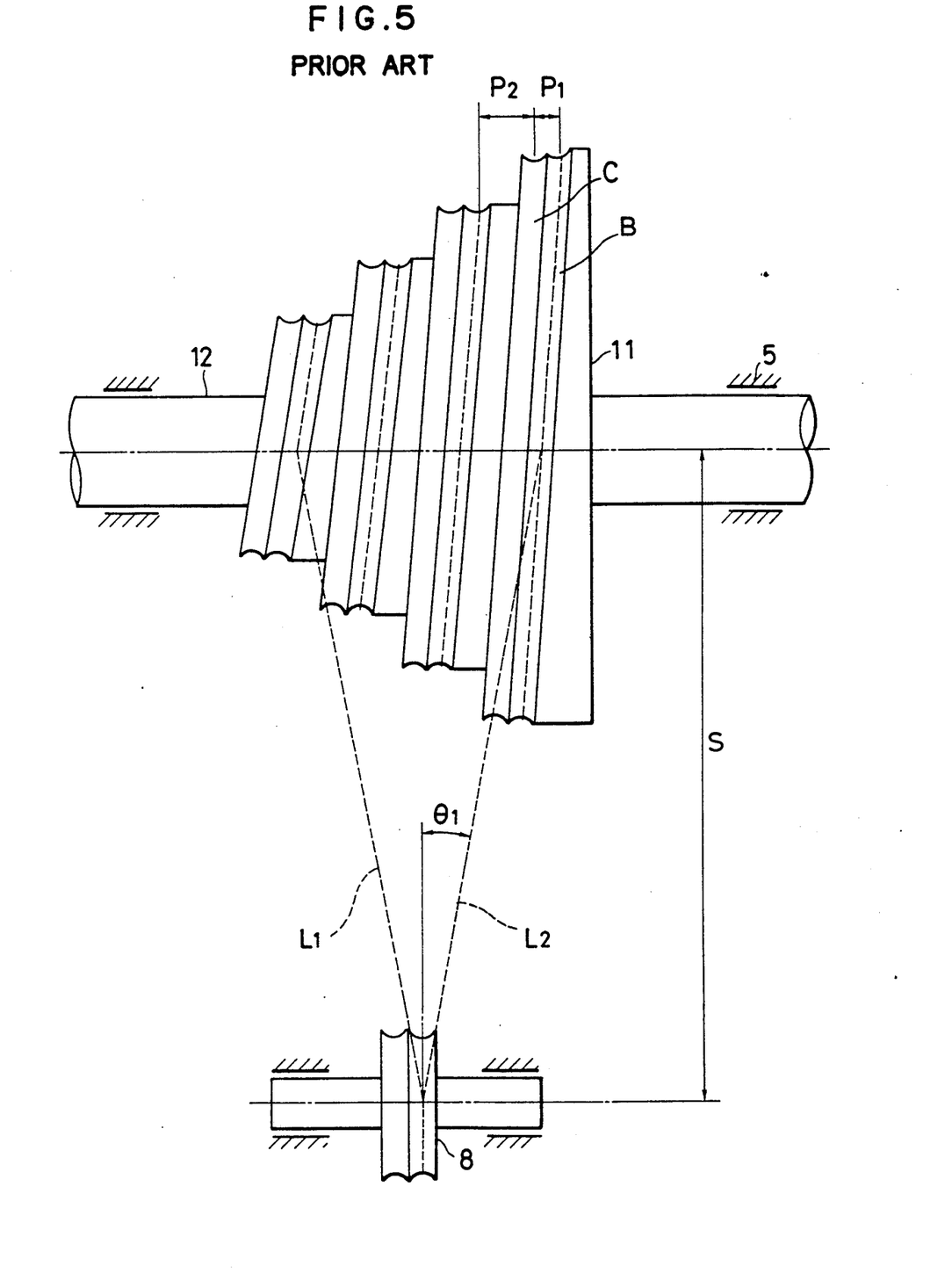
FIG. 5 is a top plan view of a corn pulley and the idler pulley of the balance mechanism of FIG. 2.

A situation for the double threaded corn pulley 11 is shown in detail in FIG. 5. Here, $L_1$ and $L_2$ indicate directions of the one of the suspension wires 6A and 6B wound along the thread B at the beginning and end of winding, respectively, while $\Theta_1$ indicates the fleet angle for this suspension wire. In FIG. 5, the other suspension wire wound along another thread C is not depicted for the sake of avoiding confusion. When the pitch between a pair of threads B and C is $P_1$, the pitch between adjacent double threads is $P_2$, the distance between the corn pulley 11 and the idler pulley 8 is S, and the winding number of the corn pulley 11 is N, the fleet angle $\Theta_1$ can be expressed as:

$$\Theta_1 = \tan^{-1}\{(P_1+P_2) \times N/2 \times 1/S\} \quad (1)$$

so that the fleet angle $\Theta_1$ increases as products of $P_1$ and $P_2$ with N increases, which is the case of the double threaded one compared with a single threaded one. Since the larger fleet angle $\Theta_1$ creates more frictional contact between the suspension wires 6A and 6B and the idler pulley 8, the durability of the suspension wires 6A and 6B becomes more restricted for the double threaded corn pulley 11.

Another problem of a conventional suspension mechanism is that the windup type springs 13A and 13B can be broken by fatigue due to repeated use. Of course the windup type springs 13A and 13B are designed to be durable enough for practical purposes, but the breaking of the windup type springs 13A and 13B in an unexpectedly short period of time is known to be caused by the use of defective material and the surface damages.

When one of the windup type spring 13A and 13B is broken, since the other one cannot maintain the balance with the suspended object 4 all by itself, the falling of the suspended object 4 results.

As already mentioned, the elimination of the possibility for such a fall of the suspended object 4 is a crucial safety requirement for an X-ray diagnostic device of type shown in FIG. 1. But, in a conventional suspension mechanism, the use of otherwise advantageous windup type springs made it difficult to eliminate possibility for the suspended object's fall due to the breaking of windup type springs.

SUMMARY OF THE INVENTION

It is therefore an object of the present invention to provide a suspension mechanism with improved safety level.

More specifically, it is an object of the present invention to provide a suspension mechanism using two suspension wires, which can avoid the shortened durability of the suspension wires.

It is another object of the present invention to provide a suspension mechanism using windup type springs, which can eliminate possibility for the fall of the suspended object due to the breaking of the windup type springs.

According to one aspect of the present invention there is provided a suspension mechanism for suspending an object to be suspended in a vertical movable manner, comprising: two suspension wires for holding the suspended object; means for changing directions of the suspension wires: two single threaded corn pulleys, one for each one of the two suspension wires, for winding the respective suspension wires passing through the changing means; and spring means for balancing against gravitational force acting on the suspended object by providing a force to rotate the corn pulleys.

According to another aspect of the present invention there is provided a suspension mechanism for suspending an object to be suspended in a vertical movable manner, comprising: suspension wires for holding the suspended object; means for winding the suspension wires; a plurality of windup type spring means for balancing against gravitational force acting on the suspended object by providing a force to rotate the winding means; means for connecting the plurality of windup type spring means such that this connecting means moves when the plurality of windup type spring means are put to be not balanced with respect to each other; and means for preventing the rotation of the winding means by detecting motion of the connecting means.

Other features and advantages of the present invention will become apparent from the following description taken in conjunction with the accompanying drawings.

DETAILED DESCRIPTION OF THE PREFERRED EMBODIMENTS

Figure 6:
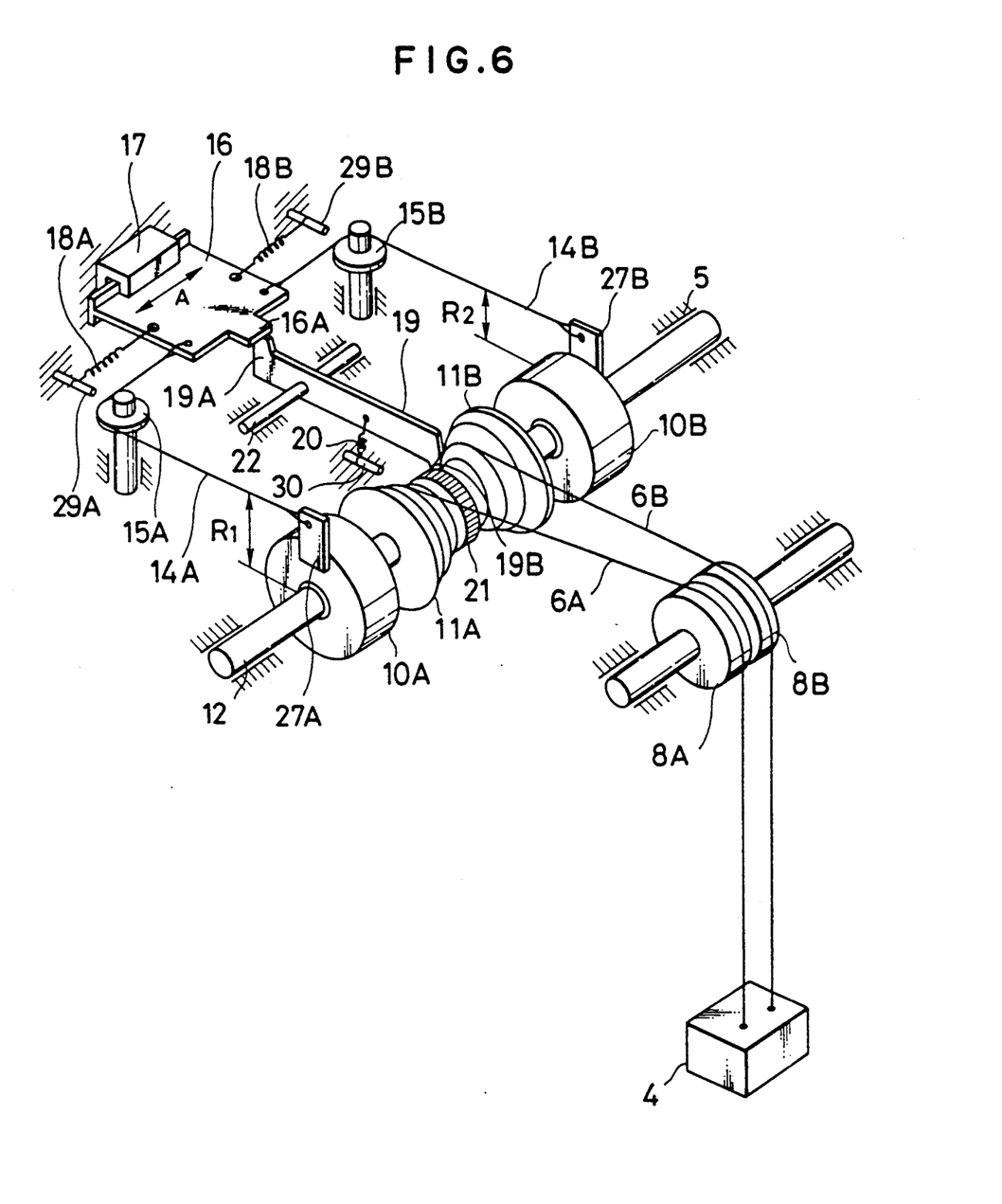
FIG. 6 is a perspective view of one embodiment of a balance mechanism for the suspension mechanism according to the present invention.

Referring now to FIG. 6, there is shown one embodiment of a balance mechanism for a suspension mechanism according to the present invention. The rest of this suspension mechanism can substantially be the same as that shown in FIG. 1 for a conventional suspension mechanism, so that their description will be omitted in the following. Also, those parts which are substantially equivalent to corresponding parts in the conventional balance mechanism shown in FIG. 2 will be given the same labels in the figures and full description of such parts will not be repeated.

In this balance mechanism, there are two main features involved.

First, there are two idler pulleys 8A and 8B, and two corn pulleys 11A and 11B, provided for each of the two suspension wires 6A and 6B, respectively.

Secondly, there is provided an additional mechanism for preventing the suspended object 4 from falling when one of the windup type springs 13A and 13B (not shown in FIG. 6) contained inside the left and right barrels 10A and 10B is broken. This additional mechanism is, as will be described in detail below, comprised of a gear 21 provided on the shaft 12 between the left and right corn pulleys 11A and 11B, wires 14A and 14B with one ends attached to the fixing members 27A and 27B, a plate 16 having an extended piece 16A and to which the other ends of the wires 14A and 14B are attached through pulleys 15A and 15B and which is also bound to the frame 5 by springs 18A and 18B and pins 29A and 29B, a block 17 for slidably supporting the plate 16 against the frame 5, a lever 19 which is supported against the frame 5 by a sub-shaft 22 and which is also bound to the frame 5 by spring 20 and pin 30, with one end 19A engaged with the extended piece 16A of the plate 16 while the other end 19B projecting over the gear 21 so that when the one end 19A is disengaged from the extended piece 16A the other end 19B and the gear 21 will be engaged.

For the sake of clarity, the following explanation will be given for these two features separately, which can be asembled together as in FIG. 6 to give a complete balance mechanism for the suspension mechanism according to the present invention.

Figure 7:
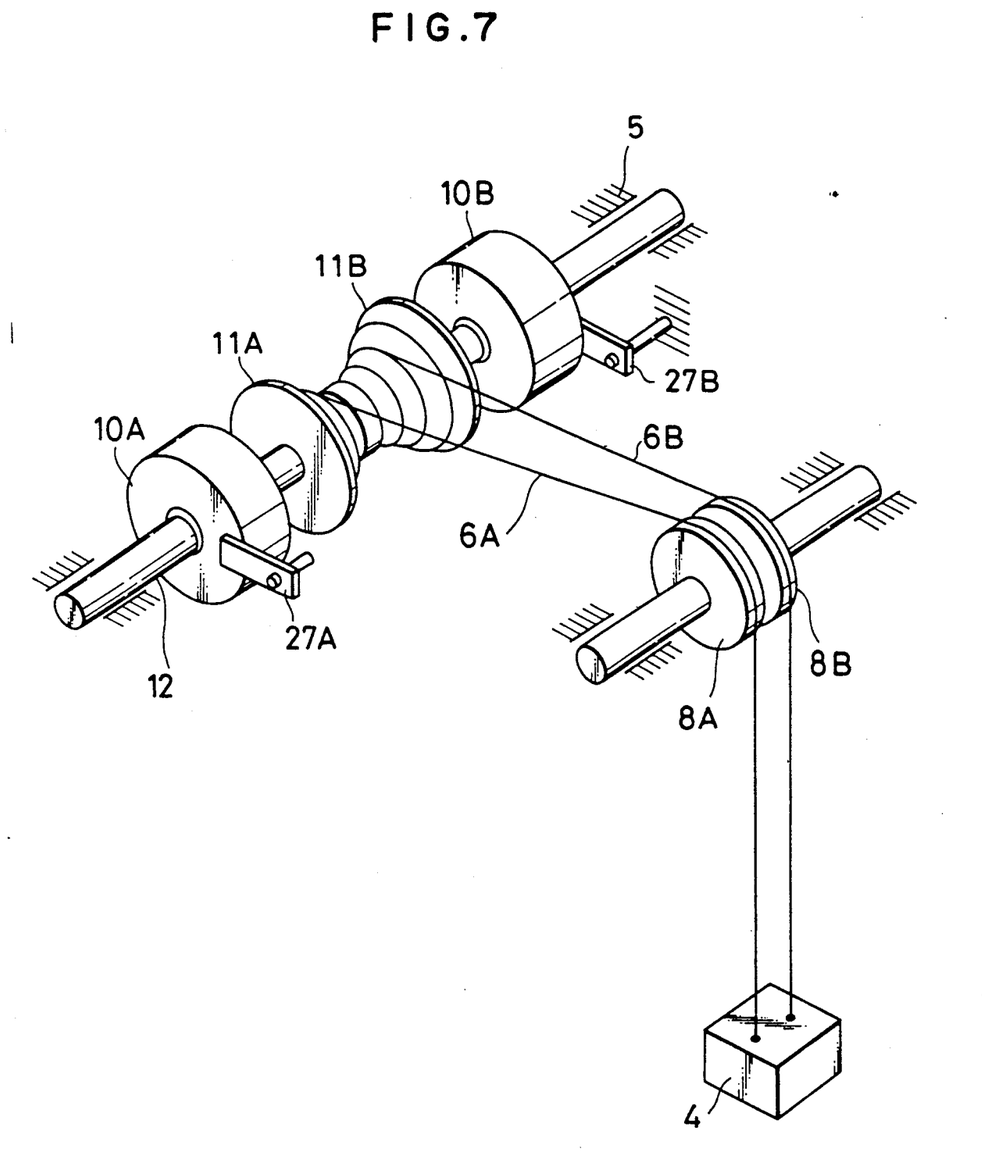
FIG. 7 is a limited perspective view of one aspect of the balance mechanism of FIG. 6.
Figure 8:
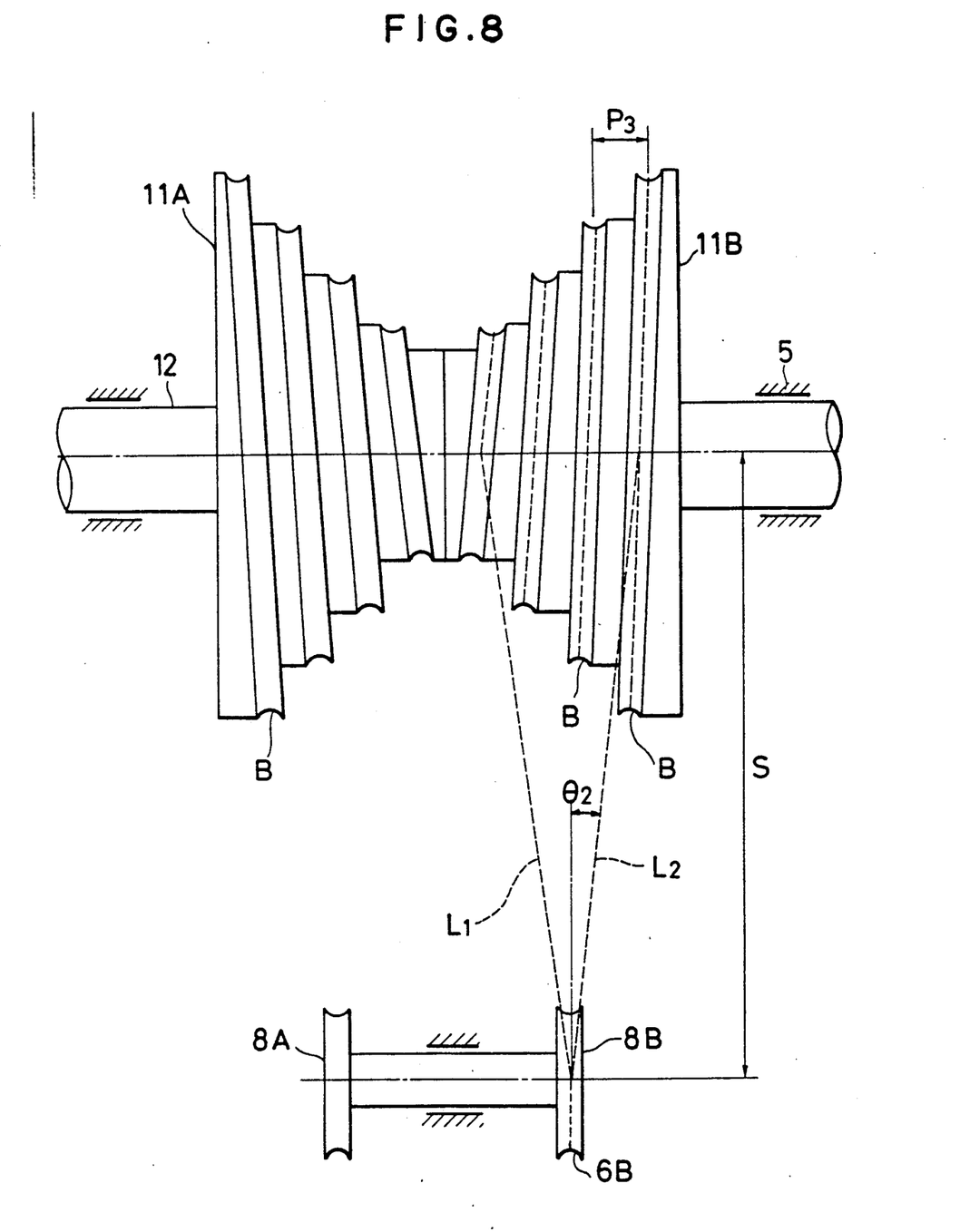
FIG. 8 is a top plan view of a corn pulley and the idler pulley of the balance mechanism of FIG. 6.

Thus, referring now to FIG. 7, there is shown the first main feature of the balance mechanism of FIG. 6. As mentioned above, this feature is characterized by the fact that there are two idler pulleys 8A and 8B, and two corn pulleys 11A and 11B, provided for each of the two suspension wires 6A and 6B, respectively. As can be seen from FIG. 8, the corn pulleys 11A and 11B are both single threaded, around which each of the suspension wires 6A and 6B is to be wound. Also, in this embodiment, the two corn pulleys 11A and 11B are arranged in an opposite direction such that smallest radii meets at a middle. FIG. 8 shows only one suspension wire 6B for the sake of clarity, but as it is obvious from FIG. 8, the situation of the other suspension wire 6A is essentially the same as that of the suspension wire 6B.

In FIG. 8, $L_1$ and $L_2$ indicate, as in FIG. 5 above, directions of the suspension wires 6B wound along the thread B at the beginning and end of winding, respectively, while $\Theta_2$ indicates the fleet angle for this suspension wire 6B. When the pitch between adjacent threads is $P_3$, the distance between the corn pulley 11B and the idler pulley 8B is S, and the winding number of the corn pulley 11B is N, the fleet angle $\Theta_2$ can be expressed as:

$$\Theta_2 = \tan^{-1}\{P_3 \times N/2 \times 1/S\} \quad (2)$$

but $P_3$ here can be substantially equal to $P_2$ used for the conventional case above, so by setting $P_2 = P_3$, the Eq. (2) becomes:

$$\Theta_2 = \tan^{-1}\{P_2 \times N/2 \times 1/S\} \quad (3)$$

Upon comparing Eq. (1) given above for the conventional case and Eq. (3), it can be seen that in this embodiment the fleet angle can be made smaller than that for the conventional case, because of the absence of the pitch $P_1$ between a pair of threads in the double threaded corn pulley.

Since the smaller fleet angle $\Theta_2$ gives rise to less frictional contact between the suspension wires 6A and 6B and the idler pulleys 8A and 8B, as much of durability of the suspension wires 6A and 6B as the conventional balance mechanism using an ordinary single threaded corn pulley can be achieved.

Thus, it is possible in this embodiment to provide a suspension mechanism using two suspension wires, which can avoid the shortened durability of the suspension wires.

It is to be noted that the fleet angle $\Theta_2$ can also be made smaller by taking a larger value for the distance S, and a smaller value for the winding number N, but there are limits in how much these can be done because the larger distance S makes a whole suspension mechanism larger and the smaller winding number N makes the stroke, i.e., a range of movement, of the suspended object 4 smaller.

Figure 9:
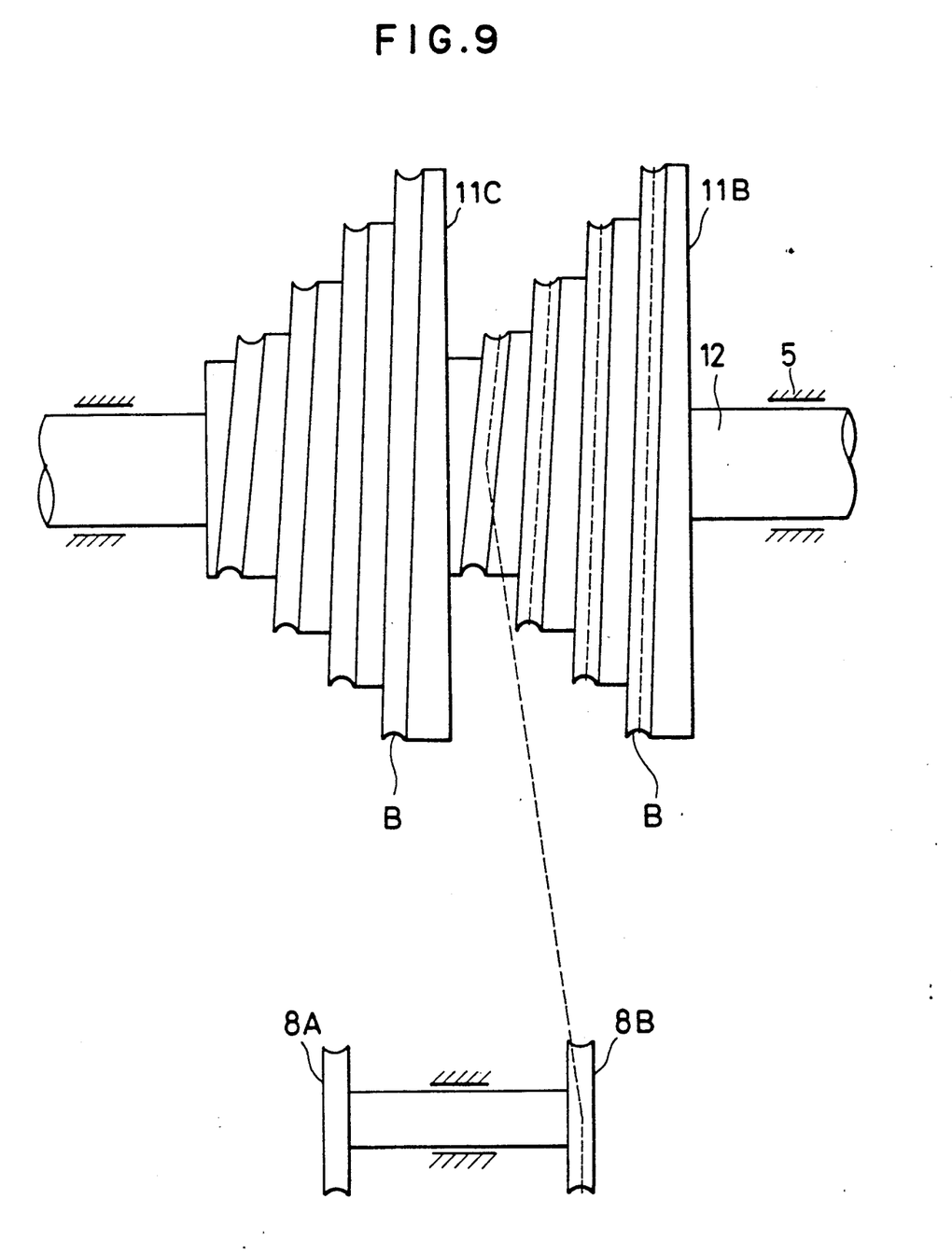
FIG. 9 is a top plan view of an alternative arrangement of the corn pulley and the idler pulley of of the balance mechanism of FIG. 6.

FIG. 9 shows a rather obvious alternative configuration of two corn pulleys 11A and 11B in which the corn pulleys 11A and 11B are arranged in the same direction such that on both of these the radii decreases toward the same direction. The same effect as the configuration of FIG. 8 can be achieved by this configuration.

There is also another obvious variation regarding the configuration of the corn pulleys 11A and 11B, in which the corn pulleys 11A and 11B are arranged in an opposite direction such that largest radii meets at a middle, which can easily be obtained from the configuration of FIG. 8 by flipping the corn pulleys 11A and 11B by 180°. Again, the same effect as the configuration of FIG. 8 can be achieved by this configuration.

Figure 10:
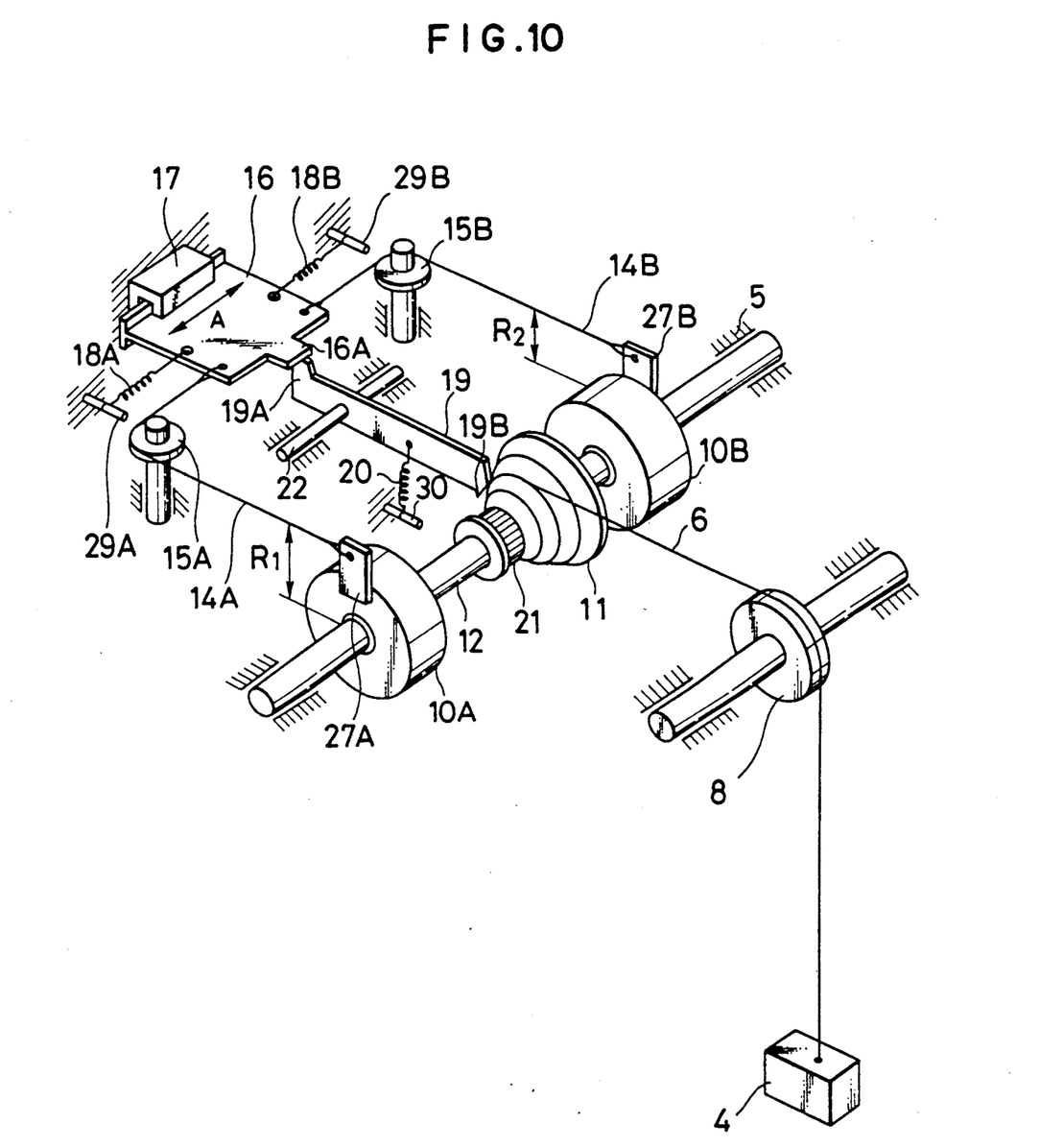
FIG. 10 is a limited perspective view of one embodiment of another aspect of the balance mechanism of FIG. 6.

Referring now to FIG. 10, there is shown one embodiment of the second main feature of the balance mechanism of FIG. 6. Here, for the sake of simplifying the figure, the first feature of two idler pulleys 8A and 8B and two corn pulleys 11A and 11B explained above is replaced by a single corn pulley 11 as in a conventional case shown in FIG. 2. As mentioned above, this second feature is characterized by the fact that there is provided an additional mechanism for preventing the suspended object 4 from falling when one of the windup type springs 13A and 13B (not shown in FIG. 6) contained inside the left and right barrels 10A and 10B is broken.

This additional mechanism is comprised of a gear 21 provided on the shaft 12 between the left and right corn pulleys 11A and 11B, wires 14A and 14B with one ends attached to the fixing members 27A and 27B, a plate 16 having an extended piece 16A and to which the other ends of the wires 14A and 14B are attached through pulleys 15A and 15B and which is also bound to the frame 5 by springs 18A and 18B and pins 29A and 29B, a block 17 for slidably supporting the plate 16 against the frame 5, a lever 19 which is supported against the frame 5 by a sub-shaft 22 and which is also bound to the frame 5 by spring 20 and pin 30, with one end 19A engaged with the extended piece 16A of the plate 16 while the other end 19B projecting over the gear 21 so that when the one end 19A is disengaged from the extended piece 16A the other end 19B and the gear 21 will be engaged.

Consequently, the plate 16 is slidable in a direction indicated by an arrow A. When the distances $R_1$ and $R_2$ between the center of the shaft 12 and the wires 14A and 14B, respectively, are equal to each other, i.e., $R_1 = R_2$, and two windup type springs 13A and 13B inside the barrels 10A and 10B are balanced with respect to each other, i.e., exerting the same amount of torque, the tension of the wires 14A and 14B acting on the plate 16 will be equal to each other so that the plate 16 will assume an equilibrium position between two springs 18A and 18B. Here, although even a slight deviation from the balanced condition between two windup type springs 13A and 13B will in principle makes the plate 16 attracted toward the one of the windup type springs 13A and 13B which is exerting greater torque, such a motion of the plate 16 will be absorbed by the springs 18A and 18B so that no apparent movement of the plate 16 appears so long as the deviation from the balanced condition is within a range given by the strength of the springs 18A and 18B.

Therefore, when the windup type springs 13A and 13B are balanced with respect to each other, the barrels 10A and 10B remain stable, just as in a conventional case in which the barrels 10A and 10B are fixed to the frame 5.

On the other hand, when the breaking of one windup type spring 13A occurs, the torque due to this broken windup type spring 13A will disappear and the plate 16 will be towed to the right in the direction of an arrow A because of the remaining torque due to the unbroken windup type spring 13B. As the plate 16 slides in the direction of an arrow A, the extended piece 16A of the plate 16 and one end 19A of the lever 19 will be disengaged, and the lever 19 will rotates around the sub-shaft 22 due to the pull by the spring 20 so that the other end 19B of the lever 19 and the gear 21 on the shaft 12 will be engaged. When the other end 19B of the lever 19 and the gear 21 on the shaft 12 is engaged, the rotation of the gear 21 is prevented and consequently the rotation of the shaft 12 connected with the gear 21 is also prevented. As a result, the corn pulley 11 will not rotates in this situation so that the suspended object 4 will not fall.

Thus, in this embodiment, the possibility for the fall of the suspended object due to the breaking of the windup type springs 13A and 13B can be eliminated. Here, the suspended object 4 will move a distance given by the time taken by the extended piece 16A to disengage from the one end 19A, which can suitably adjusted by selecting an appropriate size for the extended piece 16A.

It is obvious that when the other windup type spring 13B is broken, this mechanism also works in a similar manner to prevent the fall of the suspended object 4.

It is to be noted that this mechanism cannot prevent the fall of the suspended object 4 when two windup type springs 13A and 13B are broken simultaneously. However, such a possibility is sufficiently small for any practical purposes, so that the safety of the suspension mechanism is unaffected by this highly unlikely possibility. It is still possible that one of the windup type spring may be broken due to the shock caused by the breaking of another windup type spring, but in such a case there is an ample time between the breaking of the one windup type spring and that of another one such that the mechanism of this embodiment can still be effectuated.

It is also to be noted that the location of the gear 21 between the left and right corn pulleys 11A and 11B is not essential so long as it is on the shaft 12 such that the gear 21 and of the left and right corn pulleys 11A and 11B are coacting in their rotation.

There are several possible variations of the embodiment of FIG. 10 just described. Some of such variations will now be described with references to FIGS. 11 to 13.

Figure 11:
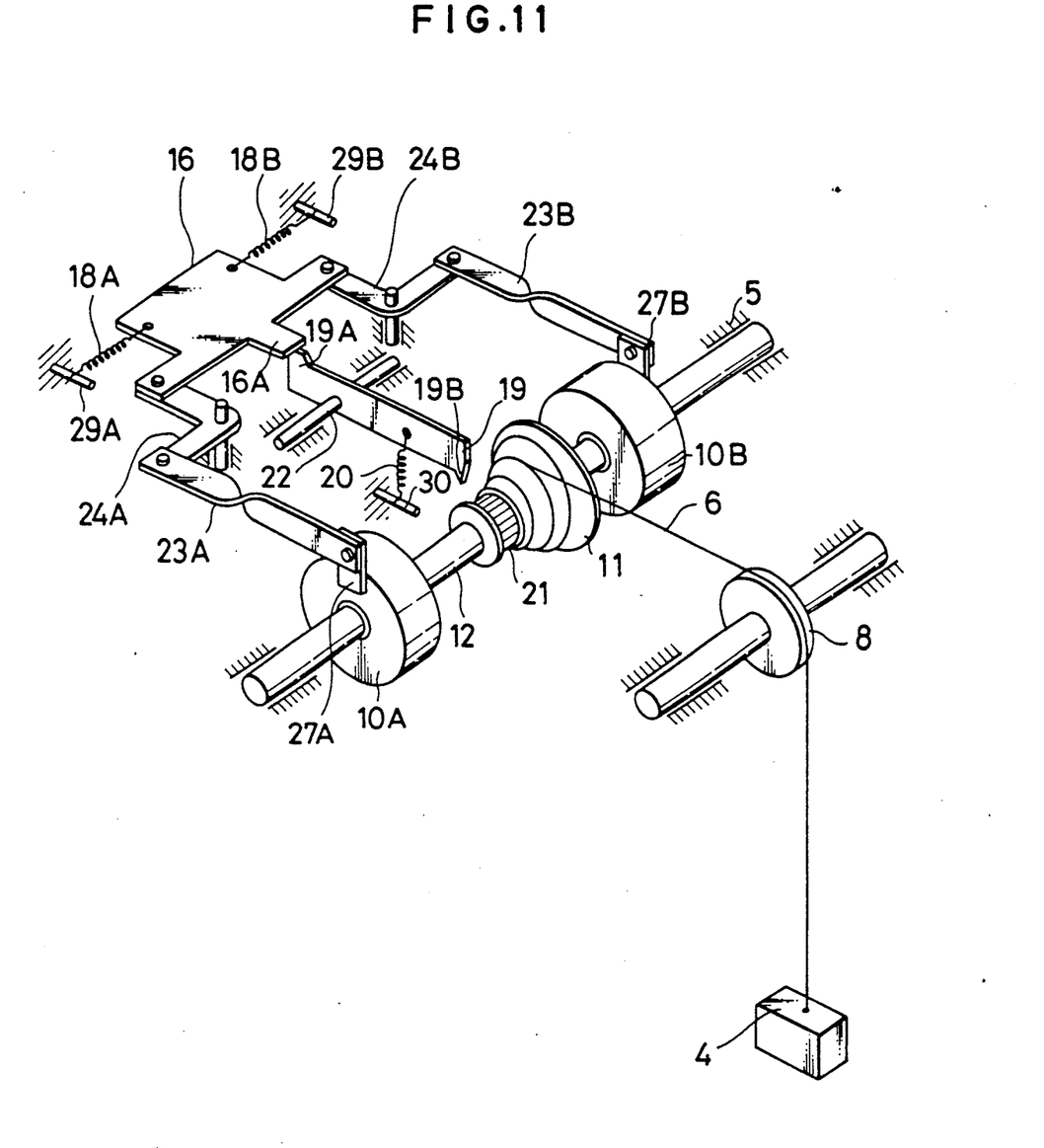
FIG. 11 is a limited perspective view of another embodiment of another aspect of the balance mechanism of FIG. 6.

FIG. 11 shows a second embodiment of the second main feature of the balance mechanism, in which the wires 14A and 14B connecting the fixing members 27A and 27B with the plate 16 through the pulleys 15A and 15B are replaced by combinations of left link plates 23A and 24A, and of right link plates 23B and 24B, respectively. The same effect as the configuration of FIG. 10 can be achieved by this configuration.

Figure 12:
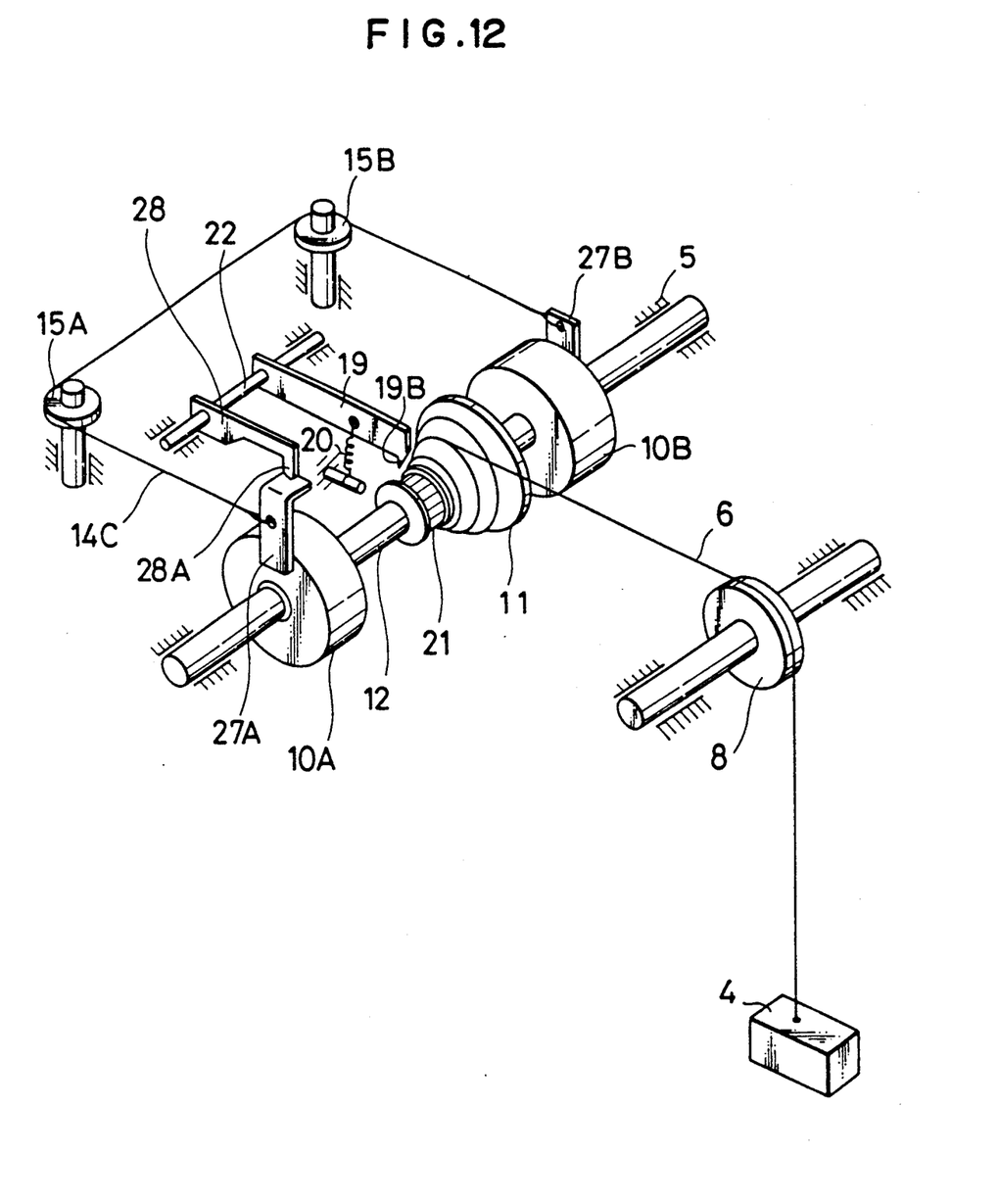
FIG. 12 is a limited perspective view of another embodiment of another aspect of the balance mechanism of FIG. 6.

FIG. 12 shows a third embodiment of the second main feature of the balance mechanism, in which the plate 16 is removed with wires 14A and 14B replaced by a single wire 14C, one end of the lever 19 is now fixed to the sub-shaft 22 while there is provided a second lever 28 with one end also fixed to the sub-shaft 22 and the other end 28A engaged with one of the fixing member 27A.

In this third embodiment, when the breaking of one windup type spring 13A occurs, the torque due to this broken windup type spring 13A will disappear and the single wire 14C will be towed to the right because of the remaining torque due to the unbroken windup type spring 13B, and then the one end 28A of the second lever 28 and one of the fixing member 27A will be disengaged, so that the lever 19 will rotates around the sub-shaft 22 due to the pull by the spring 20 such that the other end 19B of the lever 19 and the gear 21 on the shaft 12 will be engaged. Once this engagement of the other end 19B of the lever 19 and the gear 21 on the shaft 12 is made, the same effect as the configuration of FIG. 10 can be achieved by this configuration.

Figure 13:
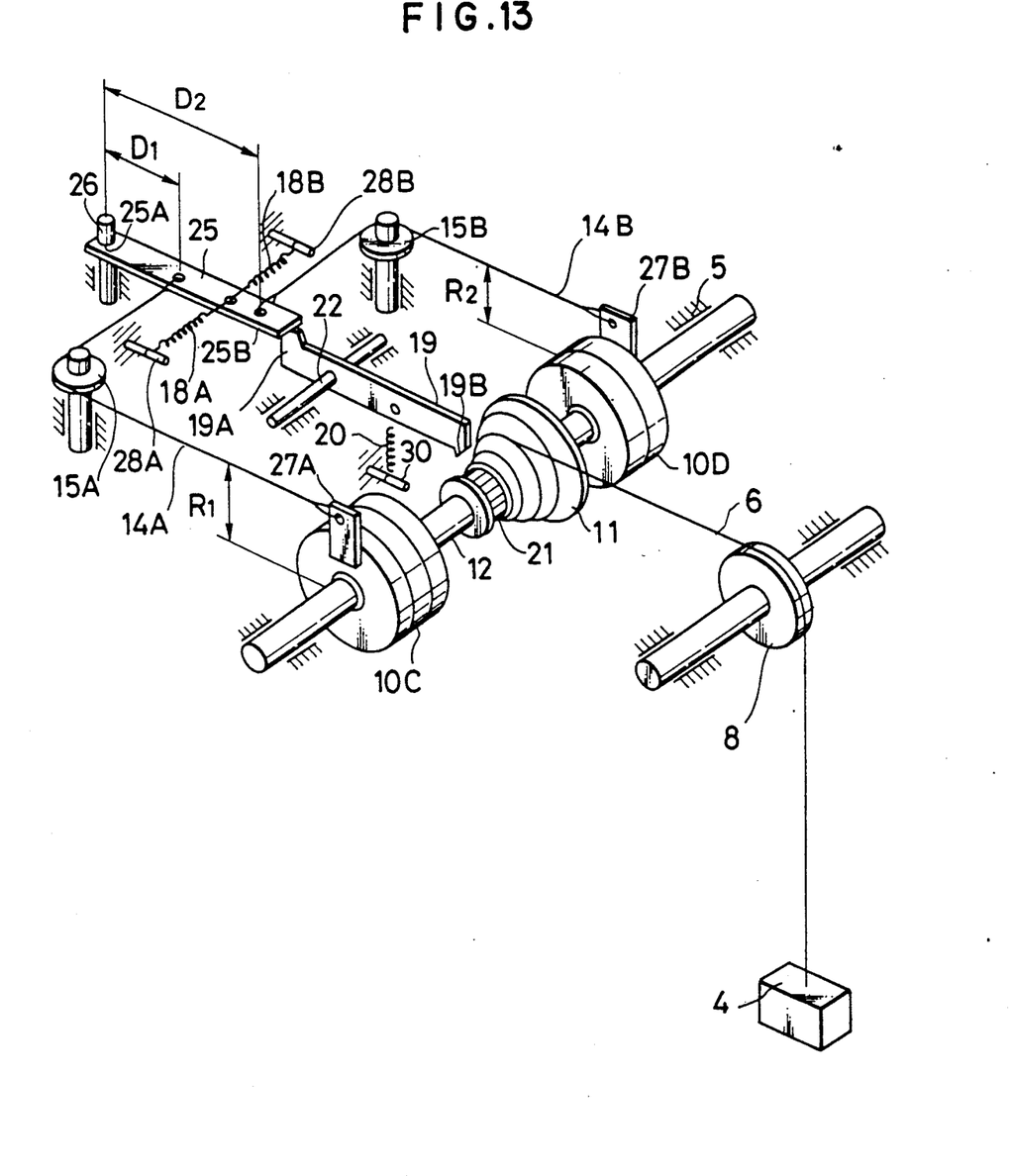
FIG. 13 is a limited perspective view of another embodiment of another aspect of the balance mechanism of FIG. 6.

FIG. 13 shows a fourth embodiment of the second main feature of the balance mechanism, in which more than two windup type springs are utilized. Here, a left-side barrel 10C contains a plurality of windup type springs to produce a torque $T_1$, while the right-side barrel 10D also contains not necessarily the same number of windup type springs to produce a torque $T_2$ smaller than $T_1$. In addition, the plate 16 is replaced by a lever plate 25 pivotally connected to the frame 5 at one end 25A through a vertical shaft 26, with another end 25B engaged with the one end 19A of the lever 19. One of the wire 14A connecting one of the fixing member 27A and the lever plate 25 through one pulley 15A is attached to the lever plate 25 at a distance $D_1$ from the vertical shaft 26, whereas another wire 14B connecting the other fixing member 27B and the lever plate 25 through another pulley 15B is attached to the lever plate 25 at another distance $D_2$ greater than $D_1$ from the vertical shaft 26.

Now, when the tension of the wires 14A and 14B are $F_1$ and $F_2$, respectively, a condition for balancing angular momenta about the vertical shaft 26 is given by:

$$F_1 \times D_1 = F_2 \times D_2$$

where $$F_1 = T_1/R_1 \text{ and } F_2 = T_2/R_2$$

with $R_1$ and $R_2$ being distances between the center of the shaft 12 and the wires 14A and 14B, respectively, as before. This implies that:

$$T_1/T_2 = (R_1/R_2) \times (D_2/D_1)$$

Thus, by suitably adjusting $R_1$, $R_2$, $D_1$, and $D_2$, the balance between left-side and right-side can be achieved.

In this fourth embodiment, when the breaking of one windup type spring in the left-side barrel 10C occurs, the torque due to this broken windup type spring will disappear and the lever plate 25 will be pulled to the right by the wire 14B because of the stronger torque due to the windup type springs in the right-side barrel 10D. As the lever plate 25 pivots around the vertical shaft 26, the end 25B of the lever plate 25 and one end 19A of the lever 19 will be disengaged, and the lever 19 will rotates around the sub-shaft 22 due to the pull by the spring 20 so that the other end 19B of the lever 19 and the gear 21 on the shaft 12 will be engaged. Once this engagement of the other end 19B of the lever 19 and the gear 21 on the shaft 12 is made, the same effect as the configuration of FIG. 10 can also be achieved by this configuration.

There is also another obvious variations of the embodiments described above, in which the wires 14A and 14B, or 14C are replaced by chains.

Besides these, many modifications and variations of these embodiments may be made without departing from novel and advantageous features of the present invention. Accordingly, all such modifications and variations are intended to be included within the scope of the appended claims.

We claim:
1. An X-ray diagnostic device, comprising:
   a bed means for supporting a patient to be diagnosed; and
   a suspension mechanism for suspending an X-ray tube in a vertically movable manner over the patient on the bed means, including:
   two suspension wires for holding the suspended object;
   changing means, one for each one of the two suspension means, for changing directions of the associate suspension wire;
   two single threaded corn pulleys, one for each one of the two suspension wires, for winding the respective suspension wires passing through the changing means; and
   spring means for balancing against a gravitational force acting on the suspended object by providing a force to rotate the corn pulleys;
   wherein the spring means comprises a plurality of windup type spring means for balancing against gravitational force acting on the suspended object by providing a force to rotate the corn pulleys, and which further comprising:

means for connecting the plurality of windup type spring means such that this connecting means moves when the plurality of windup type spring means are unbalanced with respect to each other; and means for preventing the rotation of the corn pulleys by detecting motion of the connecting means.

2. A diagnostic device of claim 1, wherein the preventing means further comprising:
an engaging means fixed to the corn pulleys:
a movable member having an engaging portion, connected with the connecting means; and
a pivotal member having first and second engaging ends, the first engaging end being engaged with the engaging portion of the movable member when the connecting means is not in motion, the second engaging end being engaged with the engaging means when the first engaging means is not engaged with the engaging portion of the movable member.

3. An X-ray diagnostic device, comprising:
a bed means for supporting a patient to be diagnosed; and
suspension mechanism for suspending an X-ray tube in a vertically movable manner over the patient on the bed means, including:
suspension wires for holding the suspended object;
means for winding the suspension wires;
a plurality of windup type spring means for balancing against a gravitational force acting on the suspended object by providing a force to rotate the winding means;
means for connecting the plurality of windup type spring means such that this connecting means moves when the plurality of windup type spring means are unbalanced with respect to each other; and
means for preventing the rotation of the winding means by detecting motion of the connecting means.

4. A diagnostic device of claim 3, wherein the preventing means further comprising:
an engaging means fixed to the winding means:
a movable member having an engaging portion, connected with the connecting means; and
a pivotal member having first and second engaging ends, the first engaging end being engaged with the engaging portion of the movable member when the connecting means is not in motion, the second engaging end being engaged with the engaging means when the first engaging means is not engaged with the engaging portion of the movable member.

5. A suspension mechanism for permitting vertical movement of a suspended object, comprising:
two suspension wires for holding the suspended object;
idler pulleys, one for each of the two suspension wires, for changing the direction of the associated suspension wire, each of the idler pulleys having a contact portion for contacting the associated suspension wire;
two single threaded corn pulleys, one for each of the two suspension wires, on which the associated suspension wire is wound and unwound when the suspended object is respectively raised and lowered, the respective suspension wires each forming a changing fleet angle with the contact portion of the associated idler pulley as the suspension wires are wound on to and off of the respective corn pulleys;
mounting means for rotatably mounting the corn pulleys; and
balancing means for balancing a gravitational force acting on the suspended object by providing a force to rotate the corn pulleys;
wherein the balancing means comprises:
a wind-up spring, having ends, associated with each of the two corn pulleys, for exerting the force to rotate the associated corn pulley, one end of each of the wind-up springs being connected to the associated corn pulley and an other end being attached to the mounting means;
connecting means for connecting the one end of each of the wind-up spring to the associated corn pulley;
a movable member attached to each of the connecting means, the movable member having a first position when the force exerted by each of the wind-up springs are balanced and a second position when the force exerted by each of the wind-up springs are unbalanced; and
preventing means for preventing rotation of the corn pulleys when the movable member is at the second position.

6. A suspension member according to claim 5, wherein the preventing means includes:
an engaging member fixed at least to the corn pulleys;
a pivotal member having a first end for engaging the engaging member when the movable member is at the second position to prevent the corn pulleys from rotating and a second end engaged by the movable member when the movable member is at the first position to prevent the first end of the pivotal member from engaging the engaging means; and
biasing means for biasing the first end of the pivotal member toward the engaging member.

* * * * *